US00PP18704P2

(12) United States Plant Patent
Zary

(10) Patent No.: US PP18,704 P2
(45) Date of Patent: Apr. 1, 2008

(54) FLORIBUNDA ROSE PLANT NAMED 'JACREFLO'

(50) Latin Name: *Rosa hybrida*
Varietal Denomination: JACreflo

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/584,127

(22) Filed: Oct. 20, 2006

(51) Int. Cl.
*A01H 5/00* (2006.01)

(52) U.S. Cl. ..... Plt./151

(58) Field of Classification Search ..... Plt./151
See application file for complete search history.

(56) References Cited

PUBLICATIONS

"Floribunda Cultivars"—Michigan State University Extension; Nov. 12, 1999, p. 1. (1 page total).*

* cited by examiner

*Primary Examiner*—Kent Bell
*Assistant Examiner*—S. B. McCormick-Ewoldt
(74) *Attorney, Agent, or Firm*—Klarquist Sparkman LLP

(57) ABSTRACT

Floribunda rose plant having very dark red flower color; resistance to powdery and downy mildew and rust; glossy foliage; compact, well branched habit; and presentation of flowers in large clusters.

1 Drawing Sheet

Figure 1:
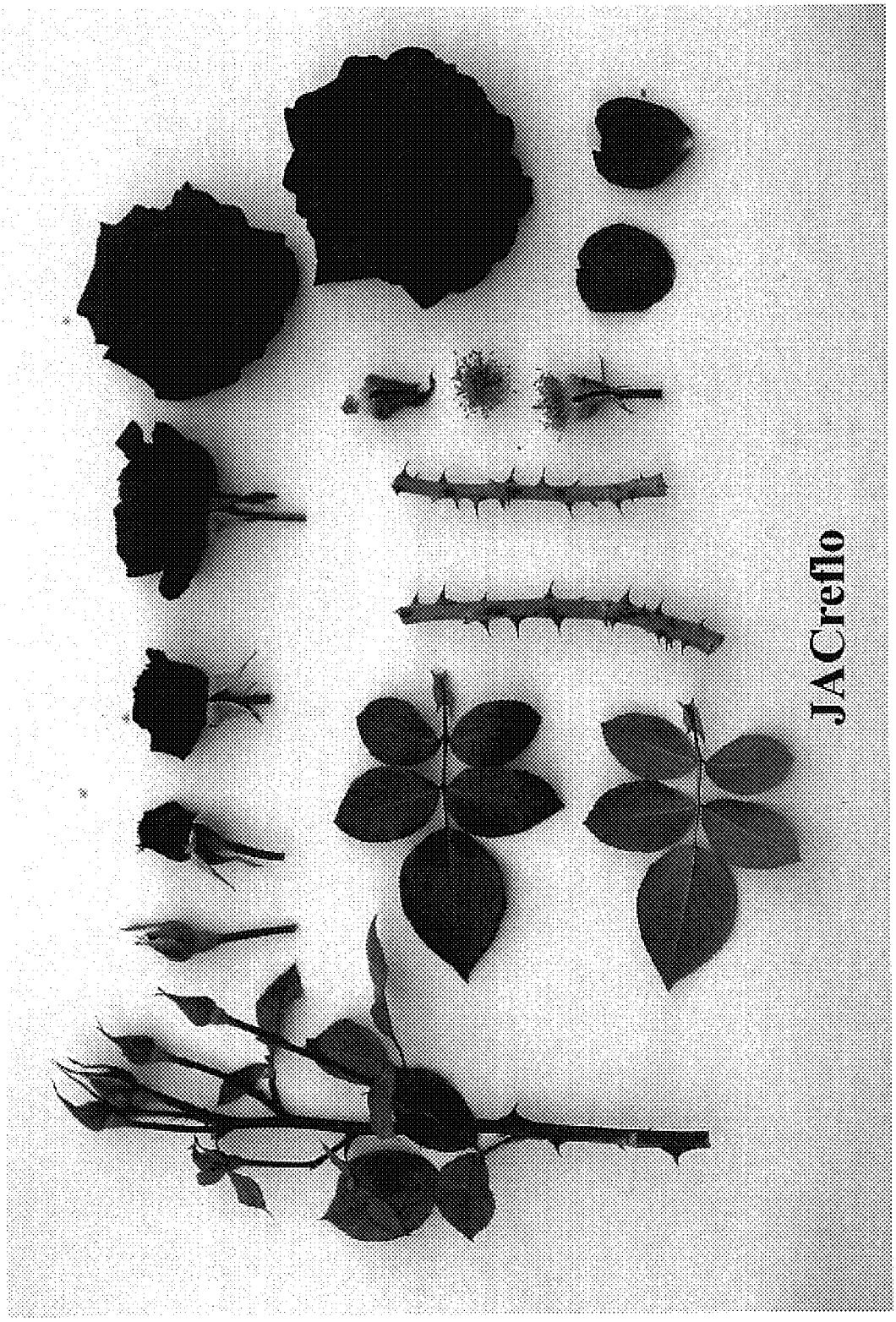

Genus and species: *Rosa hybrida.*
Variety denomination: 'JACreflo'.

ORIGIN OF THE INVENTION

The present invention relates to a new and distinct variety of a floribunda rose plant named 'JACreflo' which was originated by me by crossing the variety 'JACazle' (not patented), with the variety 'JACgloru' (not patented).

BACKGROUND OF THE INVENTION

The primary objective of this breeding was to produce a new floribunda rose variety having the compact habit, dark foliage and disease resistance of the female parent combined with the red flower color and dark glossy foliage of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Very dark red flower color.
2. Resistance to powdery and downy mildew and rust.
3. Glossy foliage.
4. Compact, well branched habit.
5. Presentation of flowers in large clusters.

Asexual reproduction of this new variety by cuttings and budding, as performed at Wasco, Calif., shows that the foregoing and all other characteristics and distinctions come true to form and are established and transmitted through succeeding propagations.

Comparison with Parents

The female parent differs from 'JACreflo' in flower color (pink versus dark red) and peta count (15 versus 25). The male parent differs from 'JACreflo' in petal count (40 versus 25) and plant habit (very upright versus compact, spreading and angular).

Comparison with Similar Variety

Other red floribundas, such as 'TANweieke' (expired U.S. Pat. No. 4,844), are much lighter in flower color.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—'JACazle' (not patented).
*Pollen parent.*—'JACgloru' (not patented).

FLOWER

Observations made from January 2005 to September 2006 from plants commencing at two years of age grown in a garden environment at Wasco and Somis, Calif.

Blooming habit: Continuous.

Bud:

*Size.*—About 20–22 mm long and 16–18 mm in diameter when the petals start to unfurl.

*Form.*—The bud form is pointed ovoid.

*Color.*—When sepals first divide, bud color is Greyed-Purple Group 187A. When half blown, the upper sides of the petals are mostly Red Group 46A and the lower sides of the petals are Red Group 53B.

*Sepals.*—Color: Upper surface: Hoary blend of Green Group 143C and Yellow-Green Group 144C. Lower surface: Yellow-Green Group 144A with occasional Greyed-Purple Group 184A overlay. Length: 30–35 mm. Width: 8–12 mm. Shape: Subulate. Surface texture: Upper: Hoary. Lower: Smooth and glandular. There are three lightly appendaged sepals. There are two unappendaged sepals with hairy edges.

*Receptacle.*—Color: Yellow-Green Group 144A. Shape: Pear. Size: Medium, about 8–10 mm long× 6–8 mm wide. Surface: Smooth.

*Peduncle.*—Length: Medium, averaging about 8–15 cm. Surface: Glandular. Color: Blend of Greyed-Purple Group 184A and Yellow-Green Group 144A. Strength: Erect.

Bloom:

*Size.*—Medium. Average open diameter is about 8–10 cm.

*Borne.*—In pyramidal clusters of 5–9 blooms.

*Stems.*—Strength: Normal. Average length is about 20–30 cm with a diameter of 8–10 mm.

*Form.*—When first open: High centered. Permanence: Outer petal edges curl slightly.

*Petalage.*—Number of petals under normal conditions: 25–30.

*Color.*—The upper sides of the inner petals are Red Group 46A with edging of Greyed-Purple Group 185A on margins. The reverse sides of the inner petals are Red Group 53B. The base of each petal upper side has Yellow Group 8C spot. The major color on the upper sides is Red Group 46A.

*Variegations.*—None observed.

*Discoloration.*—The general tonality at the end of the first day: Red Group 46A. At the end of the third day: Red Group 46A. Further aging: Color fades to Red Group 53B on day 7 and then petals drop on day 9.

*Fragrance.*—None.

Petals:

*Surface texture.*—Smooth.

*Shape.*—Obdeltoid.

*Margin.*—Smooth. Apex Shape: Emarginate. Base Shape: Cuneate.

*Form.*—Tips slightly recurved.

*Arrangement.*—Imbricated, informal.

*Petaloids.*—Number: 5. Color: Red Group 46A.

*Persistence.*—Petals drop off cleanly before drying.

*Lastingness.*—On the plant: Fair (about 5 days). As a cut flower: Fair (about 5–6 days).

Reproductive parts:

*Stamens.*—Number: 105–115. Length: 10–11 mm. Anthers: Length: 3 mm. Color: Orange Group 26C. Arrangement: Regular around styles, mixed with petaloids. Filaments: Color: Greyed-Purple Group 185D. Length: 7–8 mm. Pollen: Color: Yellow-Orange Group 22A.

*Pistils.*—Number: 55–60. Length: 5 mm. Styles: Color: Greyed-Purple Group 185D. Length: 4 mm. Stigmas: Color: Orange-White Group 159B. Length: 1 mm.

*Hips.*—None observed.

PLANT

*Form.*—Bush.

*Growth.*—Vigorous, branching, compact, spreading and angular.

*Age at maturity.*—Two years.

*Mature plant.*—Height: 105 cm. Width: 90 cm.

*Rootstock.*—Dr. Huey (unpatented).

Foliage: Number of leaflets on normal mid-stem leaves: 5.

*Size.*—Medium. About 130 mm long×105 mm wide.

*Quantity.*—Abundant.

*Color.*—New foliage: Upper side: Greyed-Red Group 178A. Lower side: Greyed-Red Group 178A. Old foliage: Upper side: Green Group 139A. Lower side: Yellow-Green Group 147B.

Leaflets:

*Size.*—About 55 mm long×43 mm wide.

*Shape.*—Ovate.

*Base shape.*—Rounded.

*Apex shape.*—Acuminate.

*Texture.*—Leathery, glossy.

*Edge.*—Serrated.

*Serrations.*—Single.

*Petiole.*—Color: Yellow-Green Group 146C.

*Petiole rachis.*—Color: Yellow-Green Group 146C. Underside: Smooth with an occasional glands.

*Auricles.*—None.

*Stipules.*—Length: 15–17 mm; serrated.

*Disease resistance.*—Resistant to downy and powdery mildew and rust and susceptible to blackspot under normal growing conditions.

*Pest resistance.*—Not observed.

*Vein color.*—Yellow-Green Group 146C.

*Venation pattern.*—Reticulate.

Wood:

*New wood.*—Color: Greyed-Purple Group 183C. Bark: Smooth.

*Old wood.*—Color: Yellow-Green Group 146A. Bark: Smooth.

Prickles:

*Quantity.*—On main canes from base: Ordinary. On laterals from main canes: Ordinary.

*Form.*—Hooked downward.

*Length.*—7 mm.

*Color when young.*—Greyed-Purple Group 183A.

*Color when mature.*—Greyed-Orange Group 164B.

Small prickles:

*Quantity.*—On main stalks: None. On laterals: None.

Winter hardiness: Hardy to Zone 5.

I claim:

1. A new and distinct variety of rose plant of the floribunda class, substantially as herein shown and described, characterized particularly by its very dark red flower color; resistance to powdery and downy mildew and rust; glossy foliage; compact, well branched habit; and presentation of flowers in large clusters.

* * * * *